(12) United States Patent
Bowman et al.

(10) Patent No.: US 10,258,274 B2
(45) Date of Patent: Apr. 16, 2019

(54) UNITARY MULTILUMEN CRANIAL BOLT

(71) Applicants: H Frederick Bowman, Needham, MA (US); Sammy M Khalifa, Cambridge, MA (US); Dean Honkonen, Groton, MA (US)

(72) Inventors: H Frederick Bowman, Needham, MA (US); Sammy M Khalifa, Cambridge, MA (US); Dean Honkonen, Groton, MA (US)

(73) Assignee: Thermal Technologies, Inc., Waltham, MA (US)

( * ) Notice: Subject to any disclaimer, the term of this patent is extended or adjusted under 35 U.S.C. 154(b) by 0 days.

(21) Appl. No.: 15/821,670

(22) Filed: Nov. 22, 2017

(65) Prior Publication Data

US 2018/0092590 A1   Apr. 5, 2018

Related U.S. Application Data

(63) Continuation of application No. 14/120,294, filed on May 14, 2014, now abandoned.

(60) Provisional application No. 61/956,959, filed on Jun. 20, 2013.

(51) Int. Cl.
*A61B 1/32*  (2006.01)
*A61B 5/00*  (2006.01)

(52) U.S. Cl.
CPC .......... *A61B 5/4064* (2013.01); *A61B 5/6852* (2013.01); *A61B 5/6865* (2013.01); *A61B 5/6868* (2013.01); *A61B 2562/046* (2013.01)

(58) Field of Classification Search
CPC ....... A61B 1/32; A61B 17/02; A61B 17/0218; A61B 17/341; A61B 17/3421; A61B 17/3423; A61B 17/3439; A61B 2017/0225; A61B 2017/3419; A61B 2017/3425; A61B 2017/3427; A61B 2017/3429; A61B 2017/3433; A61B 2017/3441; A61B 2017/3443; A61B 2017/3445; A61B 2017/3447; A61B 2017/3449; A61B 5/4064; A61B 5/6852; A61B 5/6865; A61B 5/6868; A61B 2562/046
USPC ........................................................ 600/235
See application file for complete search history.

(56) References Cited

U.S. PATENT DOCUMENTS

| | | | | |
|---|---|---|---|---|
| 3,055,370 A | * | 9/1962 | McKinney | A61B 17/32 600/567 |
| 5,257,973 A | * | 11/1993 | Villasuso | A61B 17/34 128/912 |
| 5,634,911 A | * | 6/1997 | Hermann | A61B 17/3417 604/246 |

(Continued)

*Primary Examiner* — Zade Coley
*Assistant Examiner* — Jessica Weiss
(74) *Attorney, Agent, or Firm* — James L. Neal

(57) ABSTRACT

A unitary multilumen cranial bolt for use in multimodal monitoring of a plurality of physiological parameters in brain tissue incorporates a plurality of lumens, each lumen directing a catheter borne sensor through a bore hole in the cranium and into brain tissue of a patient. The lumens are configured to cause the catheters to splay outward as they enter the cranial cavity and reach their intended depth of penetration. Each lumen is associated with a guide. The guides are adapted for use with introducers that enable fragile and/or flexible sensors to be introduced into brain tissue. Each catheter borne sensor can be positioned and repositioned within brain tissue independently of all other sensors.

5 Claims, 11 Drawing Sheets

(56) References Cited

U.S. PATENT DOCUMENTS

| | | | | |
|---|---|---|---|---|
| 6,623,490 B1* | 9/2003 | Crane | ............... | A61M 39/0247 606/108 |
| 7,604,658 B2* | 10/2009 | Wilson | ................... | A61B 5/031 606/304 |
| 2003/0040753 A1* | 2/2003 | Daum | ................ | A61B 17/3403 606/96 |
| 2004/0167543 A1* | 8/2004 | Mazzocchi | ............ | A61B 90/11 606/130 |
| 2005/0251144 A1* | 11/2005 | Wilson | ................... | A61B 5/031 606/108 |
| 2010/0241132 A1* | 9/2010 | Bobo, Sr. | ............... | A61B 5/031 606/108 |
| 2014/0066917 A1* | 3/2014 | Cosman, Jr. | ....... | A61B 18/1477 606/33 |

* cited by examiner

UNITARY MULTILUMEN CRANIAL BOLT

BACKGROUND OF THE INVENTION

Brain injury accounts for millions of injuries and thousands of deaths annually. Traumatic brain injury accounts for more than a million injuries each year in the United States alone. Brain injury also occurs in cases of subarachnoid hemorrhage which typically result from cerebral aneurysm but also may occur in connection with accidents and traumatic brain injury.

Treatment for brain injured patients must address the initial injury and the likely eventual onset of secondary ischemic brain injury. Secondary neurological injury may occur hours or even days after the initial injury. Commonly it is associated with post injury swelling of brain tissue within the confined space of the cranial cavity. It is therefore necessary to monitor various physiological parameters within brain tissue if secondary injury is to be predicted and possibly avoided or, when it occurs, most effectively treated.

The onset of secondary damage to brain tissue is difficult to predict. To address this difficulty simultaneous neuromonitoring of a number of predictive physiological parameters, termed multimodal monitoring, is used. Multimodal monitoring assesses and presents to the medical practitioner insight into the condition of the brain injured patient as indicated by the concurrent monitoring of several parameters. This facilitates the forecasting of secondary neurological injury and the treatment of brain injuries

SUMMARY OF THE INVENTION

This invention facilitates the forecasting of secondary neurological injury during treatment of brain injuries. Certain parameters when detected and monitored are instrumental in this forecasting. Examples of such parameters include intracranial pressure, cerebral blood flow (i.e.: perfusion), temperature, oxygen, and neurological parameters assessed through microdialysis and electroencephalography. Probes sensitive to parameters to be monitored are inserted into the brain tissue and provide data to appropriate monitors. Each probe comprises an elongated catheter with a sensor at or near its distal end. The sensor is adapted to sense one or more of the physiological parameters to be monitored and is introduced to the site in the brain where the parameter is to be assessed. Desired locations for a sensor vary in depth and lateral separation. Separation of the sensors in some cases is mandated to prevent crosstalk. For example, to avoid thermal contamination between sensors a temperature sensor or an oxygen sensor is located outside the thermal influence region of a heated cerebral blood flow (i.e.: perfusion) sensor.

To monitor various physiological parameters within the brain tissue of a patient, catheter borne sensors are introduced into the brain tissue through a burr hole drilled through the cranium of the patient. To direct the sensors to the intended locations a multilumen cranial bolt is installed in the burr hole. Each lumen or channel in the cranial bolt accepts an individual probe that is adapted to monitor one or several particular parameters.

It is an object of this invention to provide a cranial bolt with one or more lumens that may be associated with a guide to facilitate the introduction of a catheter borne sensor through the lumen and into brain tissue.

It is also an object of this invention to facilitate the introduction of delicate sensors into brain tissue. Delicate sensors are those that are fragile and subject to damage when being introduced or which are so flexible that they tend to kink in the lumens through which they are to be introduced. Also, such sensors may not readily penetrate the Dura. Examples of delicate sensors are those whose function depends in part on the use of fragile membranes, such as those used to measure oxygen and those used in connection with microdialysis. A related object is to provide one or more introducers for optional use with delicate catheters and sensors. An introducer is fed through a guide, the associated lumen in the bolt and the cranial bore in order to conduct the delicate catheter borne sensor through the guide, the lumen and the skull bore and into brain tissue without causing the catheter to kink or the delicate sensor to be damaged.

It is an object of this invention to provide a unitary multilumen cranial bolt in which are formed lumens that exit the distal end of the bolt along divergent paths so that catheters introduced through the lumens diverge within the brain tissue and position catheter mounted sensors at disparate locations within the brain.

It is another object of this invention to minimize the size and number of burr holes. To this end, in multimodality monitoring, a plurality of probes are introduced through a single cranial bolt installed in a burr hole. Multiple channels or lumens extend through the bolt with each channel having a proximal end situated to be outside the skull cavity when the bolt is installed and a distal end open to the cranial cavity.

A further object of this invention is to provide users the ability to adjust and readjust the depth of one or more catheter insertions independently of the fixation-in-place of other catheters.

The cranial bolt has a solid, unitary body defining a relatively broad proximal portion that narrows to a smaller distal portion defining a shank shaped to enter and engage the burr hole. Multiple lumens are formed through the solid, unitary body between the proximal end and the distal end of the unitary body. Having multiple lumens extending through a unitary, solid body simplifies construction and use, reduces cost and optimizes sensor orientation and separation.

Particularly, the unitary structure facilitates introduction of the bolt into the skull opening with the rotary axis of the bolt normal to the surface of the skull. This properly aligns the lumens for receiving the insertion of catheter borne sensors.

To minimize the size of the burr hole to be drilled in the skull of a patient it is necessary to minimize the width of the shank of the cranial bolt. Yet, in a multilumen bolt, all the lumens must pass through the shank. Minimization of the width of the shank is accomplished by having a plurality of lumens (three, four or five for example) converge within the body of the bolt from disparate locations in the relatively broad proximal end of the bolt to pass through the narrow shank of the bolt in close proximity to each other. Each lumen has a proximal end situated outside the cranial wall when the device is in use and a distal end at the distal end of the shank to access the interior of the cranial wall when the device is in use. The lumens converge from the disparate locations in the proximal end of the bolt to close proximity in the small distal end of the bolt or shank without intersecting. The zone or locus at which the lumens reach their closest proximity, each lumen having minimal separation from adjacent lumens, is termed the nadir of convergence. This is in the shank and typically would be at or near the distal end of the shank.

Convergence of the lumens toward a nadir in the shank, without more, does not produce the desired separation in the brain tissue of catheter borne sensors introduced through the lumens. Catheters introduced into brain tissue are to be oriented along divergent paths to separate the sensors from each other. To achieve this the lumens are skewed with respect to the central axis of the bolt. This establishes divergent paths for catheters introduced through the lumens so the catheters splay outward, away from each other, as they penetrate brain tissue. The separation of the proximal ends of the lumens at the proximal end of the bolt and the skewed orientation of the lumens in the bolt result in a configuration that affords comfortable working separation for the medical practitioner when introducing catheters into the lumens and separation in the brain tissue of sensors introduced through the lumens.

To orient the lumens so as to provide divergent paths for catheters, the cranial bolt is constructed with the distal ends of the lumens angularly displaced with respect to the proximal ends of the lumens about the central (i.e.: rotary) axis of a threaded shank. This produces for the lumens a skewed path through the bolt relative to the central axis. The skew and the convergence of the lumens can provide the largest separation available for a given diameter of the threaded shank.

The angle of rotation existing between the proximal and distal ends of any particular lumen is such that the particular lumen would intersect in the bolt the path an adjacent lumen would take if the distal end of the adjacent lumen were not also rotated with respect to its proximal end. Restated, the skew of the lumens relative to the central axis of the bolt is such that each lumen intersects in the unitary body the path that an adjacent lumen would take as the lumens converge if the distal end of the adjacent lumen were not also angularly displaced with respect to its proximal end.

In a preferred embodiment, the separation of each one of the lumens from adjacent lumens in the nadir of convergence is not more than the diameter of the larger of the one lumen and the adjacent lumens and not substantially less than 0.01 inch. An acceptable minimal separation in a bolt formed of a unitary mass of titanium is 0.009 inch, slightly less than 0.01 inch. The minimum separation determined when the bolt is formed can be one to minimize the diameter of the shank of the bolt while preserving the structural integrity of the bolt during installation and use.

In a preferred embodiment the cranial bolt is of titanium with a plastic wing mounted on the proximal portion of the bolt, the wing being used to manually screw the bolt into a burr hole drilled in the skull of a patient. This provides MRI compatibility along with favorable manufacturing and thermal characteristics.

DETAILED DESCRIPTION OF THE DRAWINGS

Figures 1, 1A:
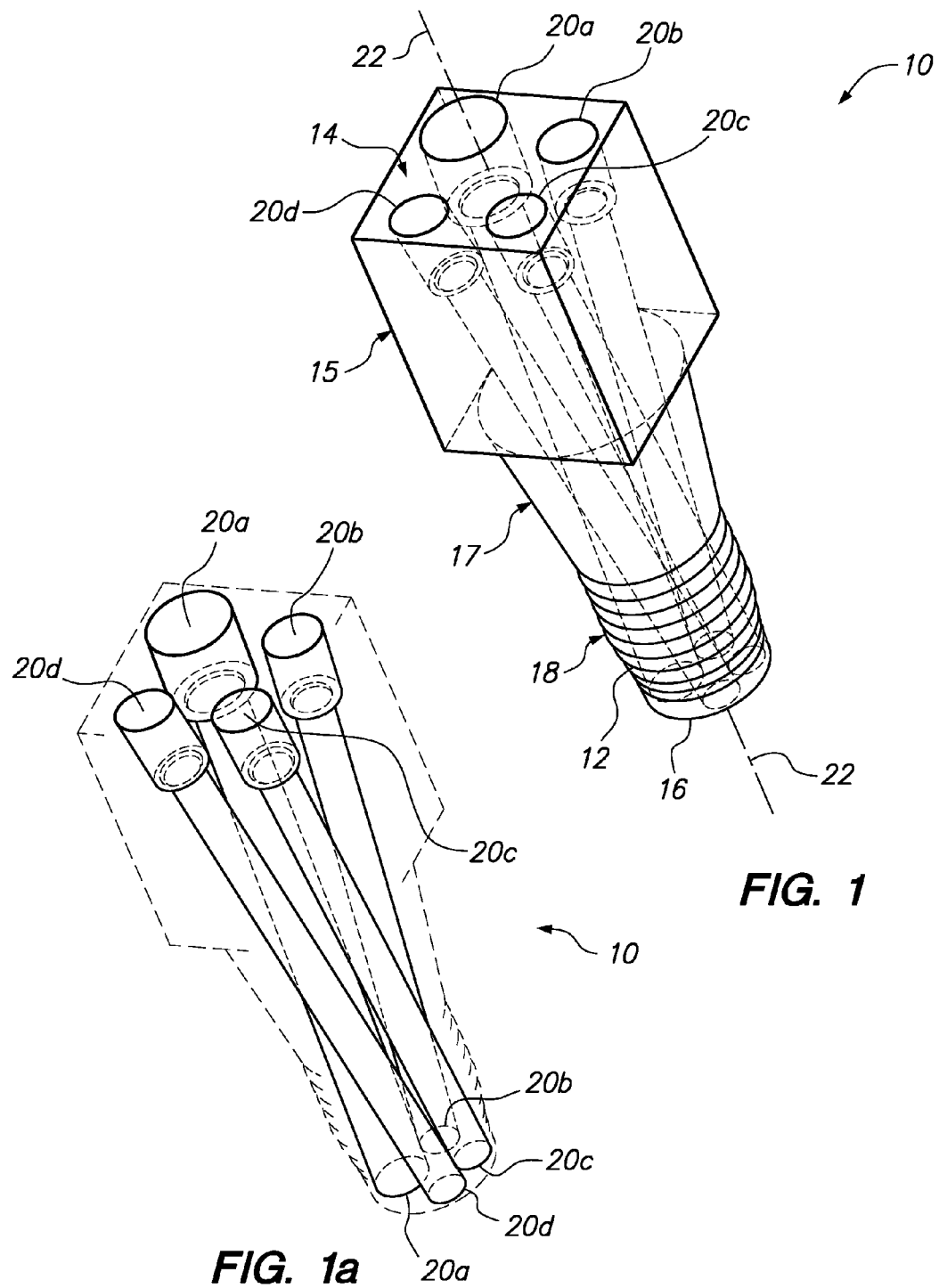
FIG. 1 is a perspective view of a cranial bolt of a preferred embodiment of this invention with the lumens through the bolt shown in dotted lines.
FIG. 1a is a perspective view of the cranial bolt of FIG. 1 showing the lumens with the body of the bolt shown in phantom.

Reference is made to FIGS. 1 and 1a. Cranial bolt 10 is formed as a unitary body with a proximal end 14 and a distal end 16. The unitary body has a proximal section 15 polygonal in cross section (in FIG. 1 a square) and a cylindrical distal section forming a shank 18 with threads 12. Between the section 15 and the shank 18 is a tapered midsection 17 (in FIG. 1 a truncated cone). Passageways or lumens 20 are formed through the unitary bolt 10 from the proximal end 14 to the distal end 16, passing through the unitary body of the bolt including the shank 18. The lumens are designated 20(a), 20(b), 20(c) and 20(d) to distinguish individual lumens in various views. (The numeral 20 without a letter designates all or multiple lumens collectively or an undifferentiated single lumen.) The lumens 20 may be alike or different. In FIG. 1, lumen 20(a) has a larger bore than the other lumens. The threaded shank 18 is adapted to engage the wall of a burr hole in a patient's skull to mount the bolt 10. The treaded shank is screwed about axis 22 into the burr hole in the skull with the threads 12 of the shank engaging the inner wall of the skull bore. Typically, when the distal end 16 of the shank 18 aligns with the inner wall of the skull the bolt is correctly positioned.

The distal ends of the lumens 20 are in communication with the cranial cavity; the proximal ends of the lumens 20 are spaced apart outside the cranial cavity and facilitate access by the medical practitioner. The lumens 20 (i.e.: the central axes of the lumens) are skewed with respect to the rotational axis 22 (See FIGS. 4(a)-4(d)) of the threaded shank 18 to define for catheters inserted through the lumens 20 divergent paths into the cranial cavity. This is achieved by forming the lumens 20 with their distal ends displaced angularly with respect to their proximal ends about the axis of rotation 22 of the threaded shank 18. The axis of rotation of the shank, also termed the central axis of the bolt 10, is the axis about which the bolt is turned as the threaded shank 18 is screwed into a burr hole in the cranium of a patient. The unitary bolt 10 may be formed of a medical grade material such as titanium.

Figure 2:
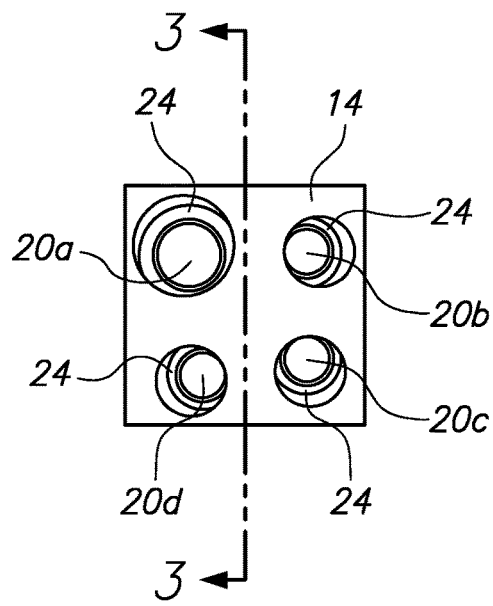
FIG. 2 is a plan view of the proximal end of the cranial bolt of FIG. 1.

In FIG. 2 the proximal end 14 of the bolt is illustrated showing the proximal ends of four lumens 20. The lumens may be of the same size or of different sizes depending on the anticipated usage. In FIG. 2 lumen 20(a) is of a larger diameter than the other three. Enlargements 24 countersunk into the proximal ends of the lumens 20 will be described in connection with FIG. 6.

Figure 3:
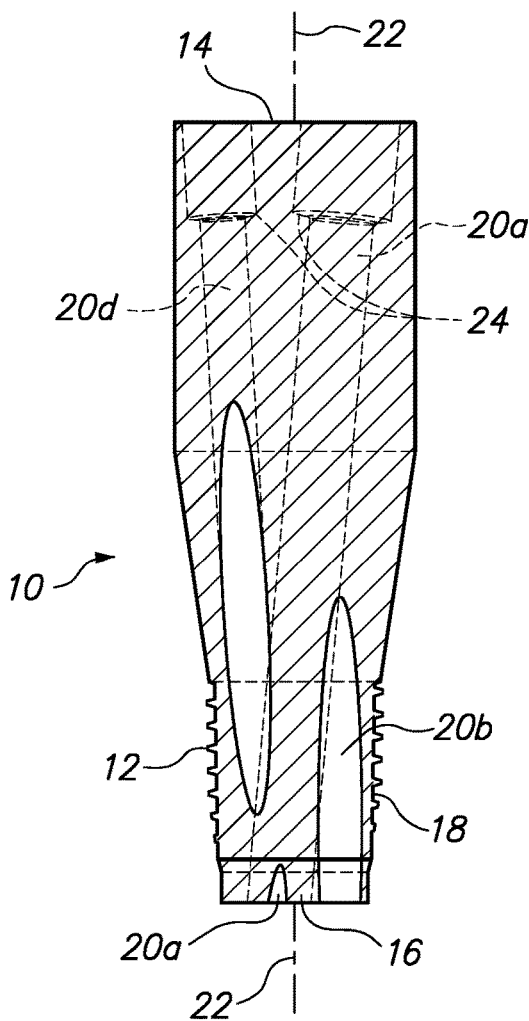
FIG. 3 is a cross-sectional view taken along line 3-3 of FIG. 2.

FIG. 3 is a cross-sectional view taken along line 3-3 of FIG. 2. The lumens all pass through the bolt 10 at skewed angles with respect to the axis of rotation 22 of the bolt 10. (In some embodiments the angles of skew may vary somewhat according to various factors including the diameters of the lumens and the dimensions of the bolt.) Lumen 20(a) is shown in dotted lines extending from the opening at the proximal end to opening at the distal end, a small portion at the distal end being cut-away in this cross-sectional view. Lumen 20(d) is shown in dotted lines extending from its opening at the proximal end to a midsection of the bolt, the remainder of the lumen including the distal end being cut-away in this cross-sectional view. A distal portion of lumen 20(b) is shown in cut-away, the remainder of the lumen including the proximal end not being shown in this cross-section. Lumen 20(c) is not seen in this view.

As seen in FIG. 1 and FIG. 3, the lumens 20 converge from their disparate proximal locations in the relatively large proximal end 14 of the bolt 10 toward each other to establish a close proximity or nadir of convergence in the relatively small cylindrical shank 18 and, in one embodiment, at the distal end 16 of the shank 18. It will be observed from FIGS. 1 and 2 that the proximal ends of the lumens (20a, 20b, 20c, and 20d) are at disparate locations in the proximal end 14 of the bolt 10, displaced radially outward from the central axis of rotation 22. From their proximal locations the lumens 20 converge inward toward each other and toward the axis 22 as they traverse the length of bolt 10 to converge in the distally located shank 18. Further, the distal ends of the lumens 20 are angularly displaced about the axis of rotation 22 with respect to the proximal ends of the lumens. The convergence of the lumens 20 toward the axis 22 and angular rotation of the lumens about the axis are such that the distal ends of the lumens 20 are nested to fit compactly together about the axis 22 in the shank 18.

Figure 4A:
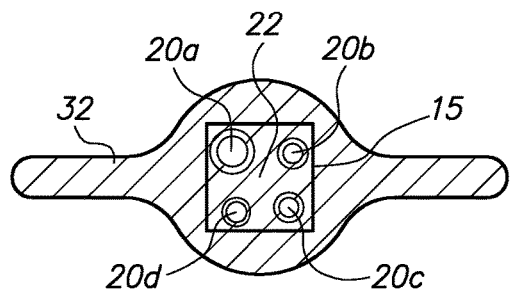
FIGS. 4(a), 4(b), 4(c) and 4(d) are cross-sectional views of FIG. 4 taken along lines a-a, b-b, c-c and d-d, respectively.
Figure 4:
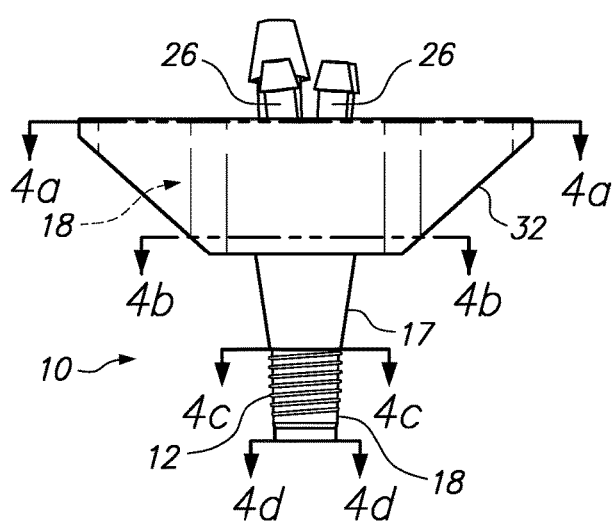
FIG. 4 is a view of the cranial bolt of FIG. 1 with certain accessory elements mounted thereon.
Figure 4B:
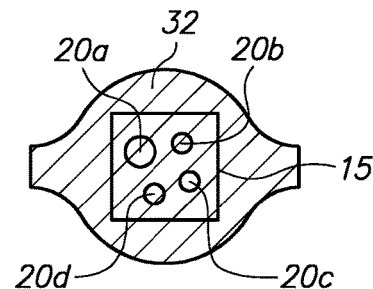
Figure 4C:
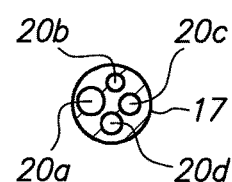
Figure 4D:
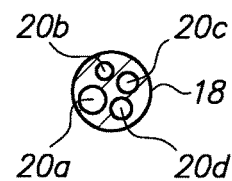

FIG. 4 shows cranial bolt 10 with connectors 26 and wing-nut element 32 (described in connection with FIG. 6) mounted thereon. Four cross-sectional views are taken along lines (a)-(a), (b)-(b), (c)-(c) and (d)-(d) of FIG. 4. These views show locations of lumens 20 as they appear at the proximal end 14 of the bolt 10 (FIG. 4a), in the proximal section 15 of the bolt (FIG. 4b), in the midsection 17 of the bolt at its junction with the shoulder of the threaded shank 18 (FIG. 4c) and at the distal end 16 of the shank (FIG. 4d). Beginning with FIG. 4(a) and continuing through the views of FIGS. 4(b), 4(c) and 4(d) the location of each lumen is advanced counterclockwise relative to the previous view. The angular displacement between FIGS. 4a and 4d of a lumen 20 is referred to as the angle of rotation of the lumen. This is described further in connection with FIGS. 5(a) and 5(b).

Figure 5A:
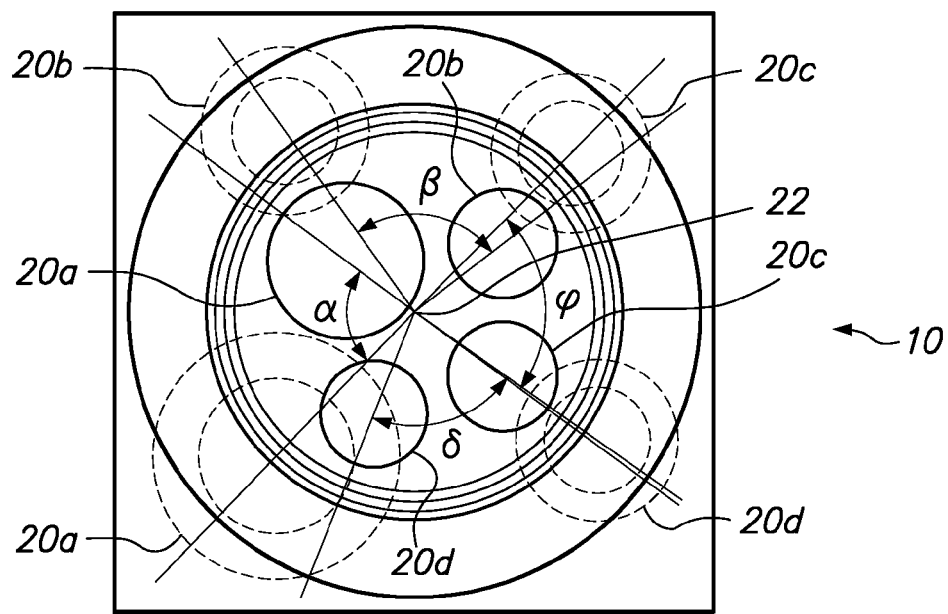
FIG. 5(a) is a distal view of a cranial bolt according to this invention showing angular displacement of proximal and distal ends of lumens extending through the cranial bolt.

FIG. 5(a) illustrates the skew introduced by the angular displacement about the central axis 22 of the distal ends of the lumens 20 relative to their proximal ends. FIG. 5(a) is a view of the bolt 10 from its distal end 16 with the distal and proximal ends of the lumens 20 shown. The distal ends of lumens 20a, 20b, 20c and 20d are shown in solid lines and the respective proximal ends are shown in dotted lines. The angle of rotation between the proximal and distal ends of lumen 20a is designated α, the angle of rotation between the proximal and distal ends of lumen 20b is designated β, the angle of rotation between the proximal and distal ends of lumen 20c is designated γ, the angle of rotation between the proximal and distal ends of lumen 20d is designated δ. To accommodate differences in the lumens the degrees of angular rotation of the distal ends of the various lumens 20 may not be exactly equal in all configurations. When the degree of angular rotation is relatively small it is not necessary for the degrees of angular rotation of the various lumens 20 to be different. However, for example, when the degree of angular rotation approaches the maximum that can be had without causing the lumens to intersect, it may be desirable to have unequal angles of displacement among the various lumens. In a bolt having lumens of different diameters an asymmetrical geometry may optimize the closeness of the lumens at the distal end of the bolt and thus enable minimization of the diameter of the shank to be achieved. That is, in a bolt with lumens of differing diameters, an individual lumen may have a different degree of angular rotation than another lumen. By way of example, viewing FIGS. 2 and 3, in the configuration shown the overall length of the bolt 10 is approximately 1.00 inch, the proximal end is 0.3185 inch square and the distal shank end is 0.228 inch in diameter; the diameter of lumen 20a is 0.132 inch and lumens 20b, 20c and 20d are each 0.059 inch diameter. In this configuration angle of rotation α is 75°. Angles of rotation β, γ and δ have angular values that may be the same or more or less than 75°. Angles of rotation are chosen to provide a desired divergence of the paths established by the lumens 20 and that minimize the diameter distal shank. All of these dimensions and proportions are by way of example. The proximal end may be of any convenient polygonal configuration, oval or circular for example. The length of the midsection 17 can conveniently be determined for various applications to provide a desired overall bolt length.

Figure 5B:
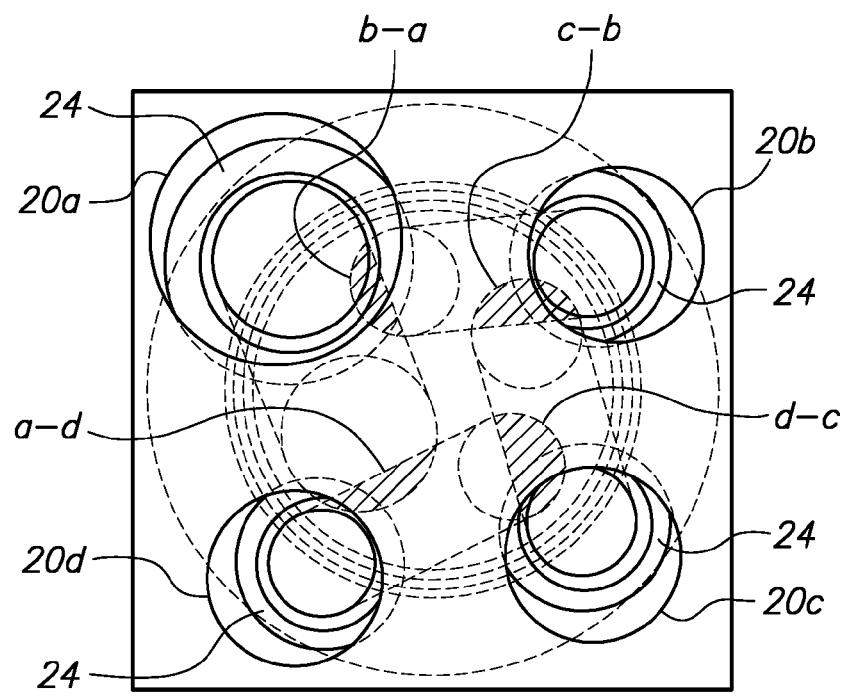
FIG. 5(b) is a proximal view of a cranial bolt of FIG. 5(a) illustrating spatial relationships of lumens extending through the cranial bolt.

FIG. 5(b) is a view of the bolt 10 of FIG. 5(a) from its proximal end 14 showing the paths formed through the bolt 10 by the lumens 20. As seen in FIG. 5(b) the path of each lumen 20 overlaps the path of an adjacent lumen and the lumens appear in this planar view to intersect. However, the lumens do not intersect. The area of apparent intersection of the lumens is shown in cross-hatch. In the planar view of FIG. 5(b) the apparent intersection of lumen 20a and 20d is shown as a-d; the apparent intersection of lumen 20d and 20c is shown as d-c; the apparent intersection of lumen 20c and 20b is shown as c-b; and the apparent intersection of lumen 20b and 20a is shown as b-a. The lumens 20 do not actually intersect because all of their distal ends are angularly displaced relative to their proximal ends. Hypothetically, if the distal end of one of the several lumens 20 were not angularly displaced relative to its proximal end, that lumen would intersect an adjacent lumen as it and the other lumens converge toward each other. The magnitude of the angular displacement of the distal ends of the lumens relative to their proximal ends is determined to provide a desired degree of divergence of the paths established by the lumens and correspondingly the desired splay for catheters introduced through the lumens, without causing the lumens to intersect.

Figure 6:
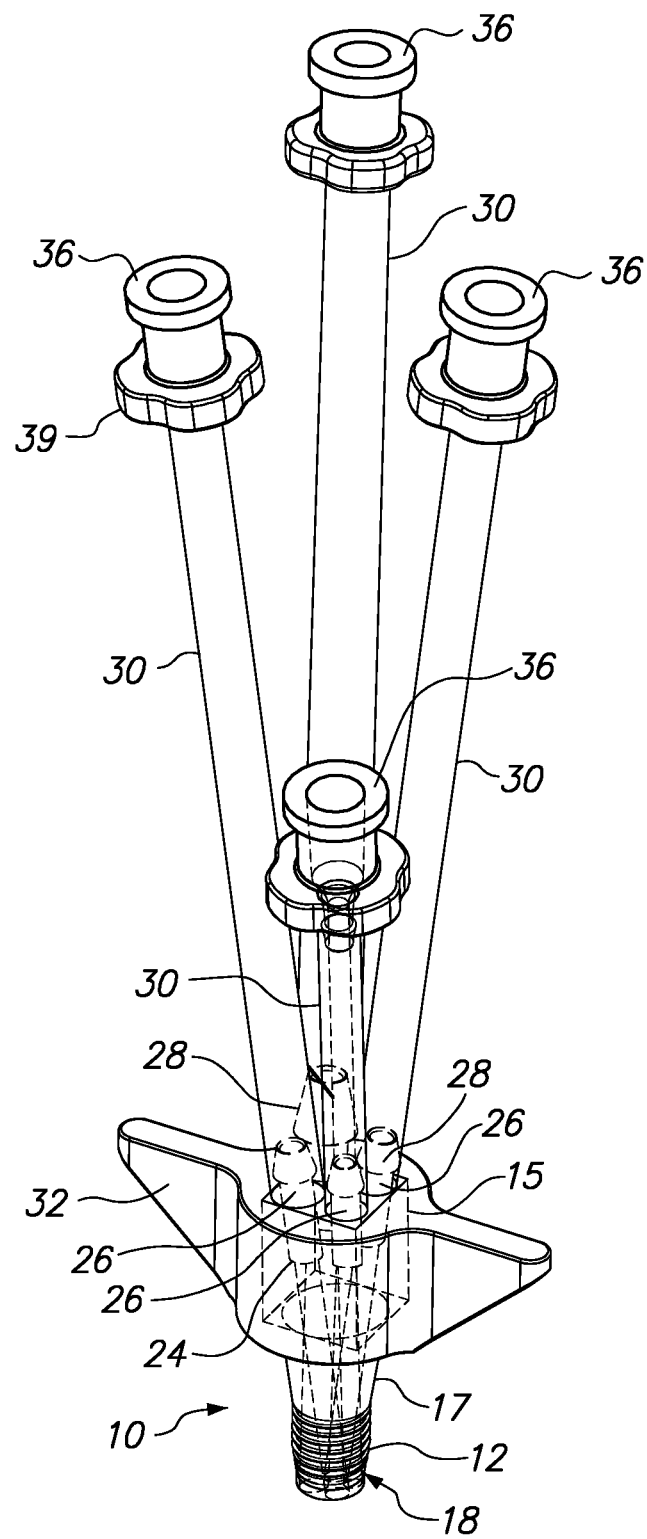
FIG. 6 is a view of the cranial bolt of FIGS. 1 and 4 with accessory elements attached.

FIG. 6 shows the cranial bolt 10 with elements to facilitate its use. Tubular guides 30 mounted on the bolt 10 extend the reach of the lumens without increasing the overall profile of the bolt 10 and serve to guide catheter borne sensors to the proximal ends of the lumens. Guides 30 are connected to the bolt 10 using connectors 26. Each lumens 20 at its proximal end has an enlarged bore 24 to form a seat for a connector 26. The connectors 26 are set within the enlarged bores 24 to mount the tubular guides 30 and have expanded zones or barbs 28 to firmly engage and hold the tubular guides 30 in place. Guides 30 may be flexible to facilitate ease of use by the medical practitioner and can be formed from polyvinyl chloride tubing. Desirably, the bore within a particular lumen 20, the bore within the mating connector 26 and the bore within the mounted tubular guide 30 are the same. The proximal ends of guides 30 are fitted with devices for fixing in place catheters that have been introduced through the guides 30. These devices may include a Luer Lock fitting 36.

The wing-nut element 32 mounted on the body of the bolt 10 is shaped to fit tightly around and be affixed to the polygonal proximal section 15 of the bolt 10. The element 32 is used to manually screw the threaded shank 18 of the bolt 10 into a burr hole in the skull of a patient. The element 32 affixed to the body of the bolt 10 obviates the requirement for installation tools. Threads 12 on the shank 18 are of the self-threading type and engage the wall of the bore drilled through the cranium. Cranial bolt threads are chosen for torque and sealing characteristics. A cranial opening no larger than 5.3 mm in diameter is desirable in some applications. This accordingly determines the diameter of the threaded shank 18. In operation a catheter with a sensor at or near its distal end is inserted through fittings 36, tubular guide 30, connector 26 and lumen 20 and into the brain tissue. When the desired depth of penetration into brain tissue is achieved the Luer Lock 36 is engaged to fix the catheter in the desired position. The system of FIG. 6 will accommodate up to four catheters, one through each lumen 20. When less than four catheters are inserted the unused lumens are sealed.

Figure 7:
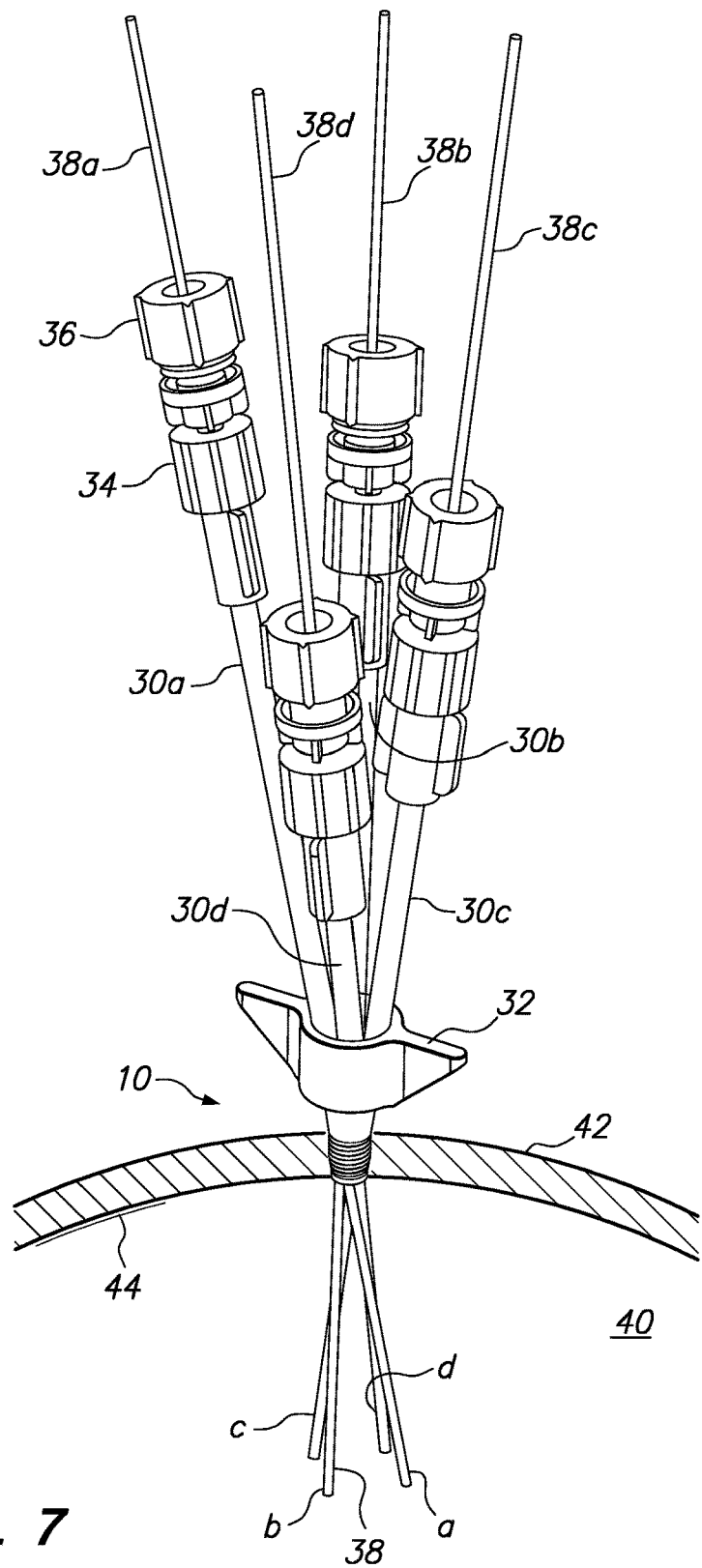
FIG. 7 shows the cranial bolt of FIG. 6 with catheters introduced into the brain of a patient.

FIG. 7 illustrates a device of the type shown in FIG. 6 installed in the skull 42 of a patient. (Elements designated by numerals 20, 30, 38, 46, 48 etc. and not followed by a letter designate all or multiple similar elements collectively or any one single element of several similar elements. Elements designated by numerals followed by a letter identify a specific one of several similar elements. For example, catheters 38a, 38b, 38c and 38d are labeled individually and in a manner to identify the proximal ends of the catheters with the corresponding distal ends.) Four catheters 38(a), 38(b), 38(c) and 38(d) extend through four respective guides 30(a), 30(b), 30(c) and 30(d), the associated lumens 20 (lumens not shown in FIG. 7) of the bolt 10 and into brain tissue 40. Each guide 30 has at its proximal end fixation elements 34 and 36 for securing in place catheters 38 that are introduced.

The fixation elements are each independent of the others so each catheter 38 is independently secured in place. Correspondingly, once catheters 38 are secured in place, any catheter can be repositioned without disrupting the placement of any other catheter. This can be significant. For example, if a catheter 38 bearing a perfusion sensor is positioned deep and near a pulsatile vessel or shallow and near the distal end of the bolt 10 it may not give an accurate result. In such a case the fixation element securing the catheter is disengaged, the depth of the catheter is adjusted until results deemed to be true are obtained and the fixation element is reengaged.

Figure 8:
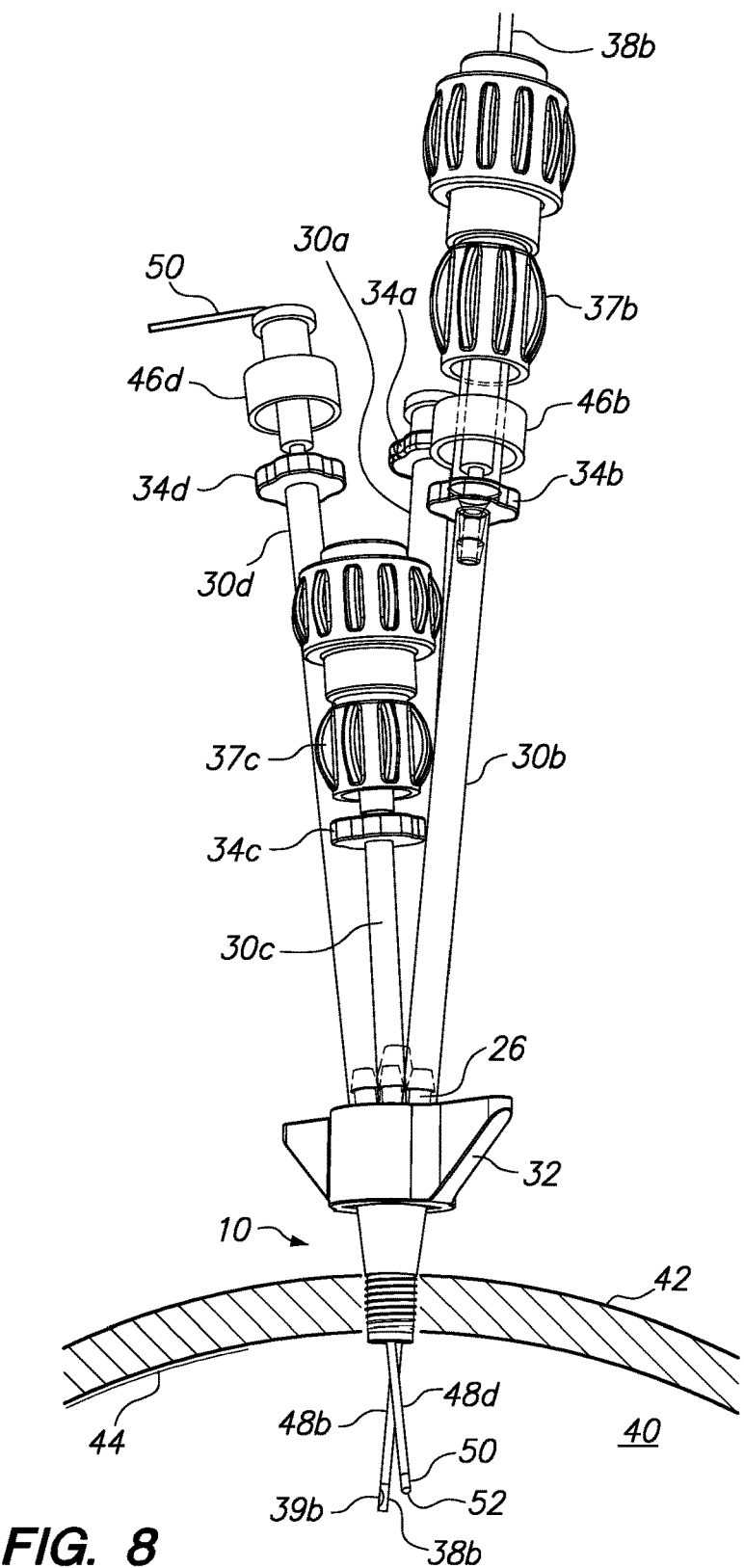
FIG. 8 is a view of the cranial bolt of FIG. 6 with one catheter introduced through a lumen into the brain of a patient using an introducer device and in another lumen an introducer is in place.

FIG. 8 shows the device of this invention with one catheter 38b installed through introducer 46b, the introducer being installed through guide 30b and the bolt 10 to access brain tissue 40. The catheter 38b is installed through the introducer 46b to enter the brain tissue 40. Sensor 39b near the distal end of the catheter 38b is in place to monitor a physiological parameter of the brain tissue 40. Either a Touhy-Borst fixation device 37b or a Luer Lock 34b is engaged to fix the catheter 38b and its sensor 39b in place. A second introducer 46d is in place to receive a second catheter through guide 30d. The introducer 46d includes a flexible, hollow tube 48d and a stylet 50. The stylet is a solid thin wire or rod that is inserted through the tube 48d when the introducer 46d is being installed. The stylet 50 extends slightly beyond the tip of the hollow tube 48d. The stylet may have a sharpened surface or other cutter 52 at its distal end to open the Dura 44 that covers the brain tissue 40 as the hollow tube 48d is inserted through the guide 30d and bolt 10 to the brain tissue 40. The stylet 50 stiffens the tube 48d to facilitate installation and fills the bore of the tube 48d to prevent brain tissue from entering the tube when it accesses brain tissue 40. When the introducer tube 48d is in place the stylet 50 is withdrawn from the tube 48d, leaving the tube 48d open to receive a catheter 38 (catheter not shown in FIG. 8). An introducer 46 is used when the catheter 38, or more likely a sensor 39 at the distal end of the catheter, is very delicate. This can occur is when a fragile or flexible sensor will not readily penetrate the Dura 44 or when an elongated flexible sensor tends to kink in the guide 30 or lumen 20. Examples of delicate (i. e.: fragile or flexible) sensors are those used to measure oxygen and those used in connection with microdialysis. In a typical installed position the distal end of the introducer tube 48 is extends into brain tissue. The extent to which an introducer tube 48 and an introduced catheter extend into brain tissue varies but frequently the depth approximates one centimeter. In FIG. 8 one tube 48b extends through guide 30b, a connector 26 and a lumen 20 (hidden) within the bolt 10. A catheter 38b is installed through the tube 48b. A second catheter 38 (not shown) is to be introduced through a tube 48d installed through the guide 30d and the associated connector 26 and lumen 20 (hidden) within the bolt 10. The stylet 50, shown in place, will be removed to admit insertion of the second catheter through the tube 48d. As an alternate to the cutter 52 being located on the stylet 50, the cutter may be formed at the distal end of the tube 48. Once a lumen is traversed and the Dura is pierced delicate sensors can be advanced into brain tissue.

If one or more introducers 46 are used it or they are placed individually after installation of the bolt 10. Referring to the example of FIG. 8, up to four catheters 38 may be installed, one through each of the guides 30. When a catheter 38 is in the intended position the Touhy-Borst fixation device 37 associated with the guide 30 through which the catheter 38 is introduced is tightened to fix the catheter 38 in the intended position. Any one catheter so positioned can be repositioned without disturbing any other catheter. If, for example, the catheter 38b is to be repositioned from an initially installed position where fixation device 37b had been employed to fix it in place, the fixation device 37b is released. The introducer tube 48b and the catheter 38b are then moved within guide 30b to increase or decrease the depth of penetration of the catheter 38b and the sensor 39b at its distal end. The outward splay of the catheter 38b changes in proportion to the change in its depth of penetration. When the sensor 39b is repositioned the fixation device 37b is reengaged to fix the introducer tube 48b and catheter 38b in the new position and to fix the sensor 39b at the new depth of penetration within the brain tissue 40. This does not disturb catheters introduced through guides 30a, 30c or 30d. The depth of penetration of each introducer tube 48 is adjusted and readjusted independently of any installed introducer or catheter. This allows users to adjust the depth of one or more catheters 38 without unlocking the fixation-in-place of other catheters. Operation to reposition a sensor when an introducer is not used is essentially the same. For example, referring again to FIG. 8, if a catheter 38 (not shown) were installed within the guide 30c without an introducer, the fixation device 37c would be released to reposition the catheter. The catheter then would be repositioned within the guide 30c to increase or decrease its depth of penetration. The fixation device 37c would be reengaged to fix the catheter in its new position.

Figures 9, 9A:
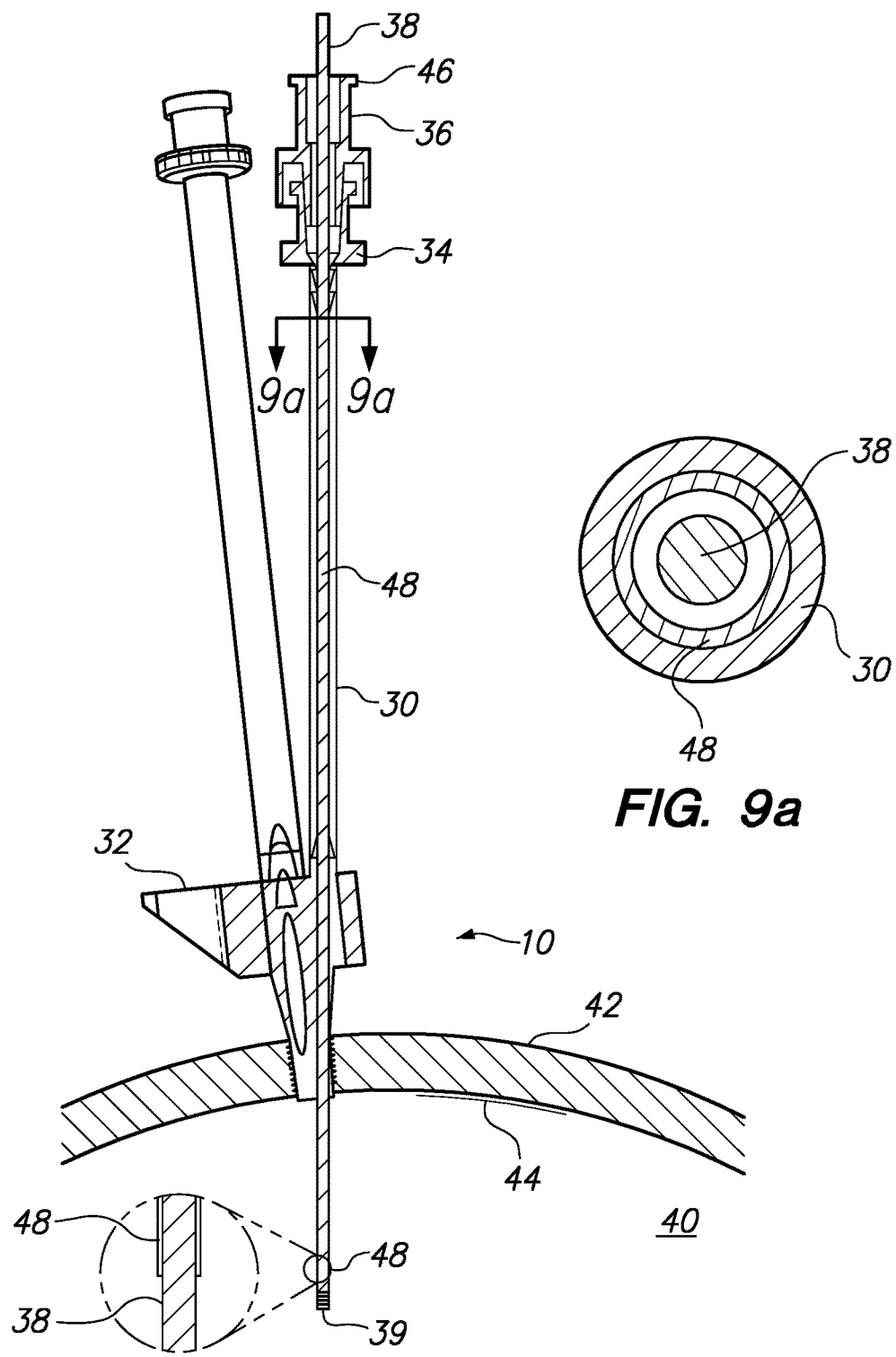
FIG. 9 is a cross-sectional view showing an introducer with a catheter introduced therethrough.
FIG. 9(a) is a cross-sectional view along line a-a of FIG. 9.

FIG. 9 is a cross-sectional view along one installed catheter 38 in which an introducer 46 is used. The catheter 38 extends through the passageway or bore within the introducer tube 48; the tube 48 extends through the guide 30. FIG. 9(a) is a cross section taken along line a-a of FIG. 9 which shows the catheter 38 within the tube 48 and the tube 48 within the guide 30. The catheter 38 does not entirely fill the tube 48 (or the guide 30 when no introducer is used) but has surrounding space. When the catheter 38 is in place with the sensor 39 at the desired location in the brain tissue 40, Luer fittings 34 are adjusted to fix the catheter and sensor in place.

Figure 10:
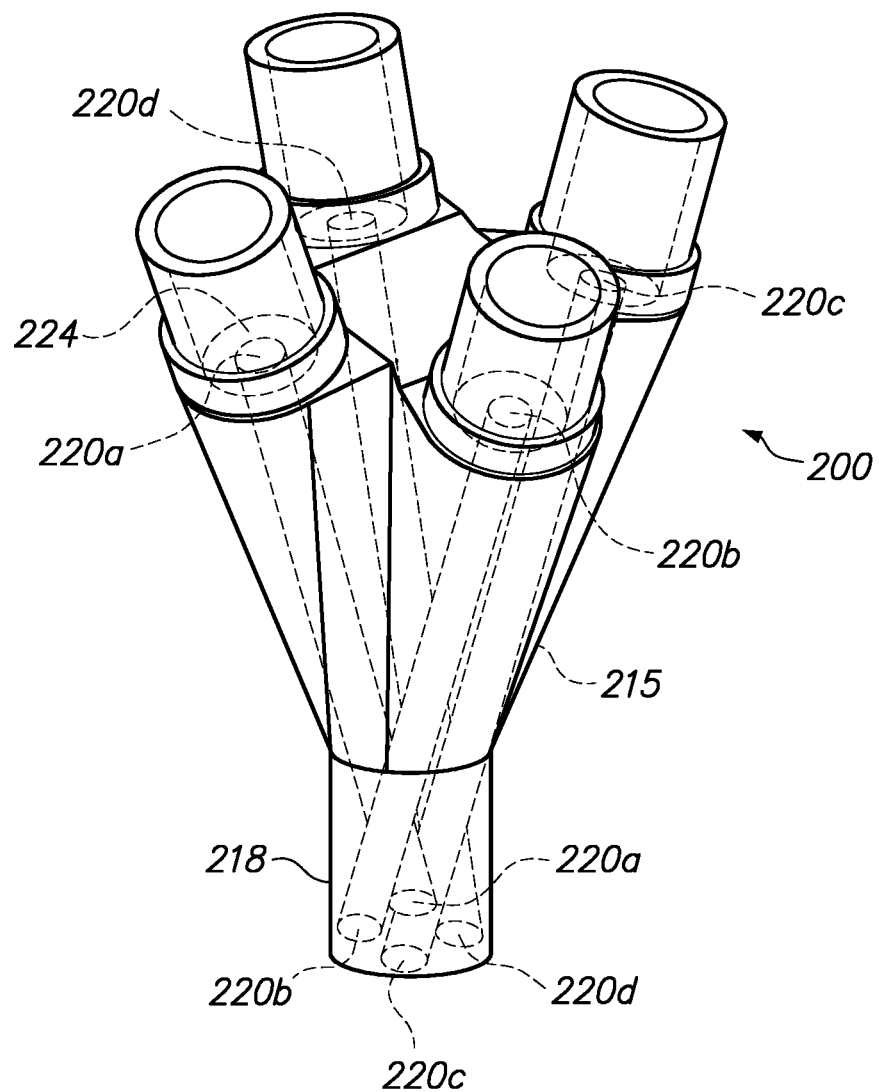
FIG. 10 shows an alternate embodiment of the cranial bolt.

FIG. 10 shows an alternate configuration of a unitary multilumen bolt 200. The unitary bolt body 215 forms a shank 218 at its distal end. Four lumens 220(a), 220(b), 20(c) and 220(d) are bored through the unitary body of the bolt 200 along paths that converge toward each other but do not intersect. The locations of the distal ends of the lumens 220 are angularly displaced with respect to their proximal ends. The lumens provide simultaneous access through the bolt 200 for four catheters. Angular displacement of the distal ends of the lumens 220 relative to their proximal ends provides divergent paths for catheters introduced through the lumens into brain tissue. The lumens 220 through the device 200 of FIG. 10 are alike, having the same diameter, and the angular displacements between the proximal and distal ends of the several lumens 220 are equal. Enlarged bores 224 at the proximal ends of lumens 220 provide secure seats for connectors 26 (not shown in FIG. 10).

Figure 11:
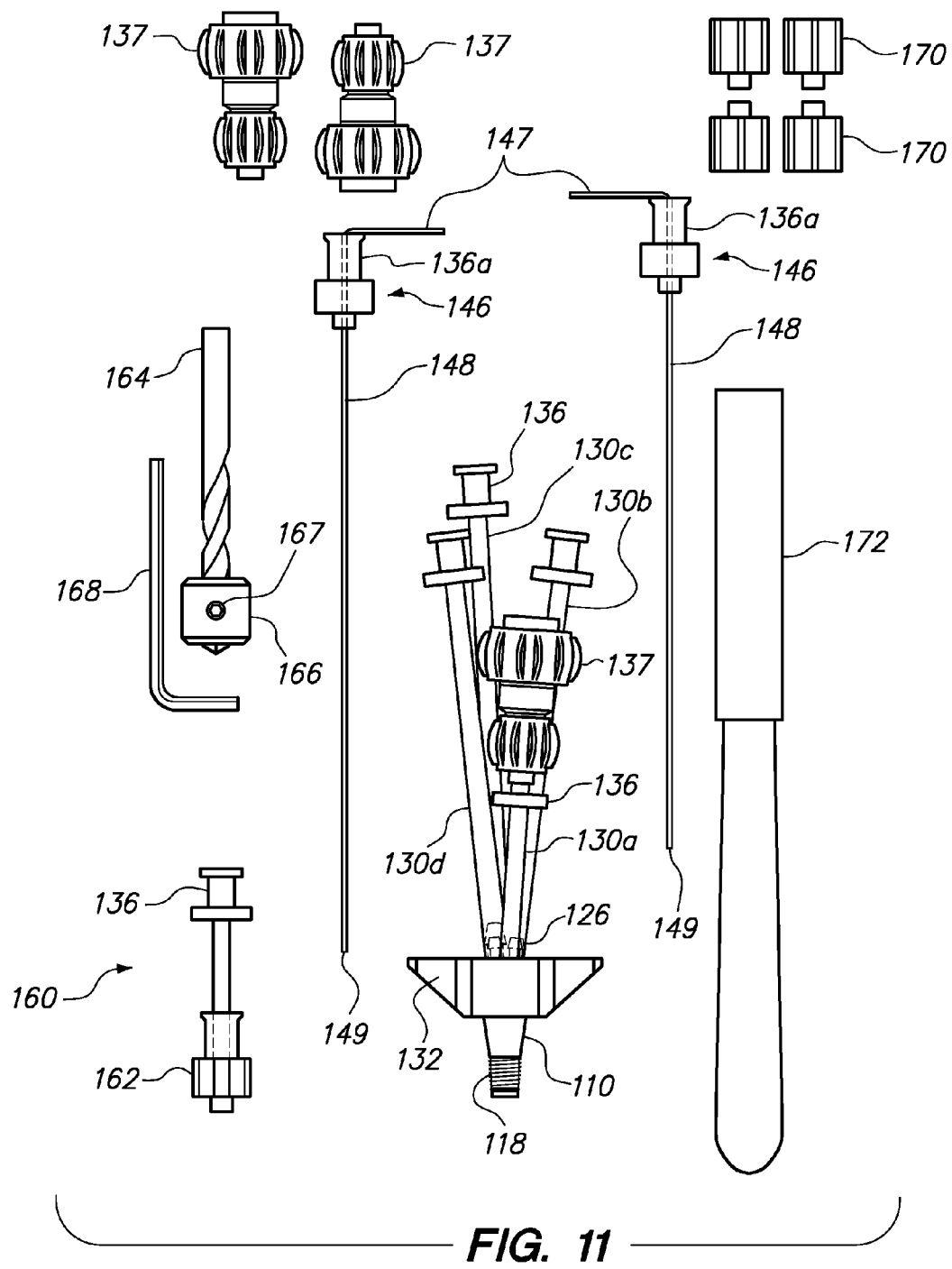
FIG. 11 shows the contents of a kit associated with the use of the cranial bolt of this invention.

FIG. 11 shows the elements of a Quad Lumen Bolt Kit. It includes instruments used to place catheter borne sensors in brain tissue during surgery or in an intensive care unit. The kit includes a unitary multi-lumen bolt 110 having a body tapered from a relatively broad, square proximal end to a relatively narrow threaded cylindrical shank 118 at a distal end. The bolt 110 is fitted with a wing-nut element 132. A guide 130 is attached to the proximal end of each lumen (hidden) in the cranial bolt 110 by means of a connector element 126. The guide 130 has a Luer fitting 136 at its proximal end. In this embodiment the guides 130 are shown of various lengths, the lengths being adapted to the anticipated need of the installing surgeon. Relatively speaking, guide 130(a) is short, guides 130(b) and 130(d) are of intermediate length and guide 130(c) is long. Two sensor introducers 146 are shown, one of length appropriate for guide 130c and one of length appropriate for guides 130(b) and 130(d). Introducers 146 can be supplied in lengths appropriate for any or all guides. Each introducer incorporates a hollow tube 148, a stylet 147 and a Luer fitting 136(a). The stylet 147 extends through the bore of the hollow tube 148 to stiffen the tube and facilitate its insertion through the guide 130 and into brain tissue. The stylet 147 substantially fills the hollow tube 148 so that, upon insertion of the tube 148 into brain, brain tissue will not advance up the bore of the hollow tube 148. The tube 148 has a sharpened end 149 capable of cutting the Dura covering brain tissue 40. The Luer fitting 136(a) is adapted to mate with a Luer fitting 136 at the distal end of a guide 130. The Luer fitting 136 on a guide 130 may also mate directly with a Luer element installed on a catheter or other device to be introduced through a guide 130. Touhy Borst compression fittings 137 provided with the kit are for optional use at the proximal ends of guides 130. A compression fitting 137 may be used to fix an installed catheter in place. A compression fitting 137, when installed on a guide 130, can also be used to seal the proximal end of the guide when, in a particular instance, it is not used. Sealing caps 170 are provided for sealing the proximal end of any unused guide 130 that is not associated with a compression fitting 137. A guide extension 160 may optionally be used when needed. The guide extension 160 has a Luer fitting 136 at its proximal end and at the opposite end a fitting 162 to mate with the Luer fitting 136 at the proximal end of a selected guide 130.

For the convenience of the surgeon the kit includes a scalpel 172 and a drill bit 164 with adjustable depth collar 166 to mark the correct drilling depth. A hex nut 167 on the depth collar and hex wrench 168 are used to adjust the position of the depth collar 166 on the drill bit 164 prior to use. The size of the drill bit 164 ensures the burr hole in the skull of a patient is correctly sized for the threaded shank 118 of the bolt 110.

The entire system has a universal aspect. Individual lumens through the bolt 110, guides 130, optional introducers 146, Luer fittings 136 and compression fittings 137 are not dedicated to a particular sensor or catheter but are broadly and very nearly universally applicable. This facilitates use in a wide range of multimodality monitoring events and provides the medical practitioner with a broad range of choices during use.

Figure 12:
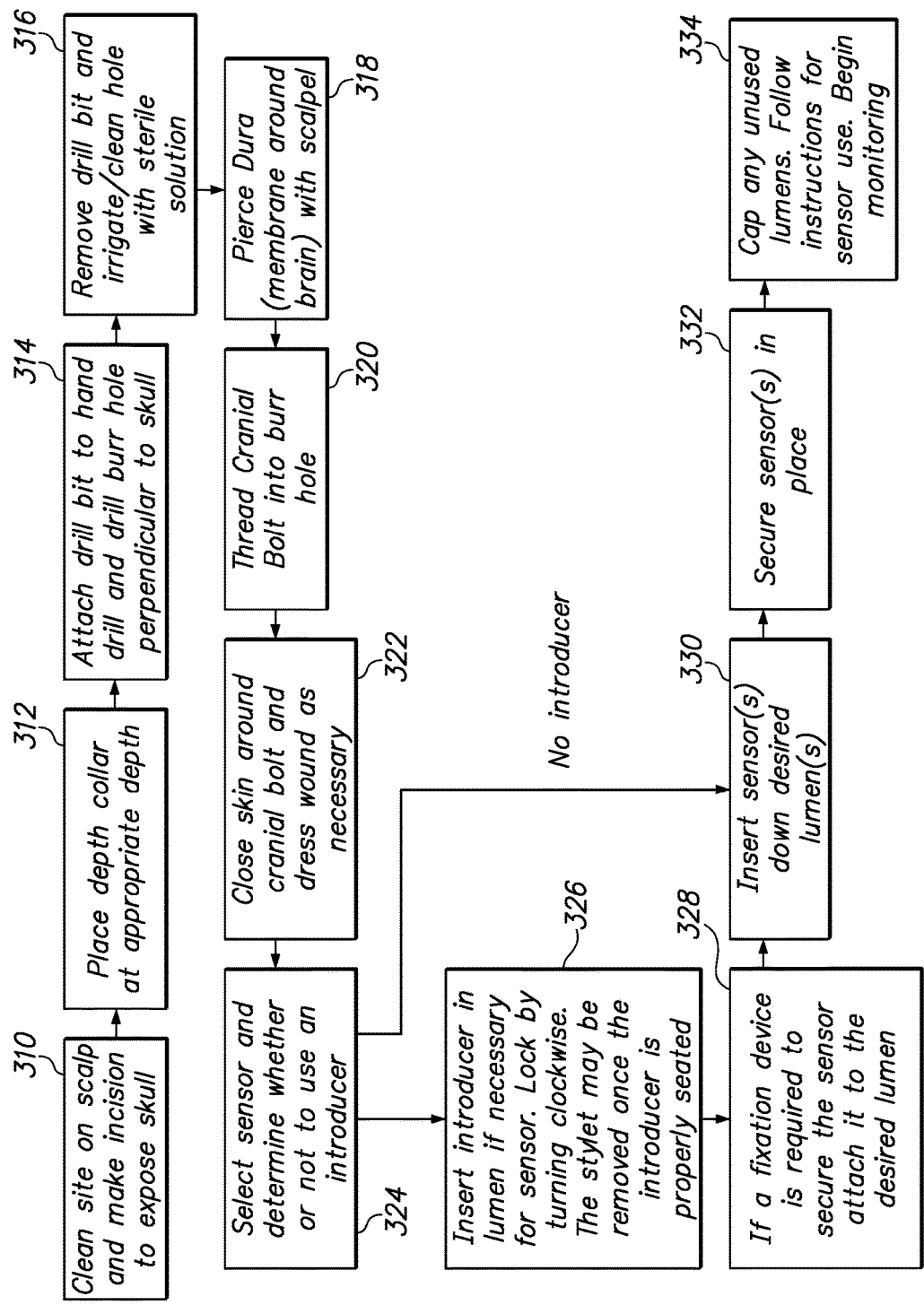
FIG. 12 is a flow chart identifying steps associated with installation and use of the cranial bolt of this invention.

The flow chart of FIG. 12 illustrates a protocol for installing the cranial bolt 10. The bolt introduction site is prepared and an appropriate scalp incision is made. The scalp is retracted so the skull is exposed. (Step 310) The hex wrench 168 and hex nut 167 are used to secure the depth collar 166 at the appropriate position on the drill bit 164 to mark the intended drill depth. (Step 312) The drill bit 164 is mounted in an appropriate drill (not shown) to drill at the insertion site a burr hole perpendicular (i.e.: normal) to the surface of the skull. (Step 314) When drilled to the intended depth the drill is removed (Step 316) and Dura surrounding the brain tissue may be pierced in cruciate fashion with the included scalpel 172 or the Dura may be pierced later in the procedure. (Step 318) The cranial blot 110 is manually threaded into the burr hole in the skull until the threads of the shank 118 are fully seated or until a depth is reached which in the surgeon's judgment corresponds to the thickness of the skull. The cranial bolt 110 is manually screwed clockwise into the burr hole using the wing nut element 132 mounted on the bolt. When the bolt is installed the proximal end of the threaded shank 118 should approximately align with the inner surface of the skull. (Step 320) After implantation the scalp incision is closed and sutured around the bolt and the wound site is dressed. (Step 322) A probe with associated sensor is selected. The chosen sensor corresponds to a physiological parameter to be monitored and a determination is made as to whether an introducer 146 is needed for the chosen probe. (Step 324) Some probes, for example a perfusion probe (i.e.: cerebral blood flow probe), are sufficiently robust that they can be inserted without using an introducer 146. Such a perfusion probe is the Q Flow 500™ Perfusion Probe from Hemedex, Inc., Cambridge, Mass., USA.

In the case of a robust probe introduced without an introducer 146, the probe is introduced directly through a guide 130 and a lumen of bolt 110. (Step 330) For example, the probe may be introduced through the short guide 130(a) and through the associated lumen within the bolt 110 into contact with brain tissue. (See FIGS. 1-4 for views of lumens 20 through the cranial bolt 10. The lumens through bolts 10 and 110 are the same or similar.) A perfusion probe frequently penetrates about 2.0-3.0 cm. from the distal end of shank 118 into the brain tissue although other depths may be selected by the surgeon. The perfusion probe consists mainly of a catheter with a perfusion sensor at the distal end. Insertion depth for the sensor can be gauged by cm. markings on the catheter. The Touhy Borst compression fitting 137 at the proximal end of the guide 130(*a*) is tightened by turning its cap clockwise to secure the perfusion probe in place. (Step 332) The perfusion probe is sufficiently robust that it may pierce the Dura if that was not a part of the bolt installation protocol. Additional perfusion probes and/or other probes may be inserted through other guides 130 and the associated lumens in the bolt 110. A sealing cap 170 is used to seal any unused guide 130. Monitoring of selected parameters by the installed sensors begins. (Step 334)

In the case of a probe with a delicate sensor or a catheter that tends to flex, kink or jam inside a guide 130 or inside a lumen through the bolt 110, an introducer 146 is used. For example, oxygen sensors and sensors used for neurological parameters may involve a delicate membrane lacking sufficient rigidity to pierce the Dura. When an introducer 146 is used, the hollow tube 148 of the introducer, with a stylet 147 inside the tube bore, is passed through a selected guide 130 and its associated lumen. The stylet 147 fills the bore of the hollow tube 148 and extends slightly beyond the tip of the tube. The stylet may have a sharpened end 149 which can be used to penetrate the Dura 44 if that is not a part of the procedure for installing of the bolt 110. The Luer fitting 136(*a*) of the introducer 146 is engaged with the fitting 136 of the guide 130. The stylet 147 is then withdrawn from the hollow tube 148; (Step 326) this hollow tube 148 then constitutes a receptor a delicate catheter borne sensor. A catheter securing device 137, if needed, is mounted on the fitting 136 of the selected guide 130 (Step 328). The delicate sensor is then extended through the tube 148 and placed in the desired location within the brain tissue. (Step 330) The compression fitting 137 is tightened to secure the sensor in place. (Step 332) A sealing cap 170 is used to seal any unused guide 130. Monitoring of selected parameters by the installed sensors begins. (Step 334)

The sensors chosen must be of the appropriate size for the guide selected. In one example, referring to FIG. 11: guide 130(*a*) has an inner diameter of 0.054 inch and extends 2.6 inches from the distal end of the bolt; guide 130(*b*) has an inner diameter of 0.043 inch and extends 4.2 inches from the distal end of the bolt; guide 130(*c*) has an inner diameter of 0.080 inch and extends 4.7 inches from the distal end of the bolt; and guide 130(*d*) has an inner diameter of 0.054 inch and extends 4.2 inches from the distal end of the bolt. If a longer guide is needed the extender 160 can be used. Luer fitting 162 of the extender engages a fitting 136 on a guide 130; the Luer element 136 on the extender 160 replacing the element 136 on the guide 130.

Catheter mounted probes that monitor various physiological parameters are introduced by means of the cranial bolts here described, one catheter per lumen. In addition to perfusion sensors, examples of catheter borne sensors that may be introduced include those for temperature, oxygen, intracranial pressure and neurological parameters assessed through microdialysis and electroencephalography. A probe sensitive to one or more of each of the parameters to be monitored is inserted into the brain tissue for providing data to an appropriate monitor. In each case a sensor is located at the site in the brain where the parameter is to be assessed.

The paths of the lumens 20 through the cranial bolt 10 described above in connection with FIGS. 1-6 or paths with similar characteristics are present in all the cranial bolts herein described and cause the probes (i.e.: the catheters and associated sensors) to splay outward and diverge as they penetrate the brain tissue. The sensors thus have lateral separations in the brain tissue that increase with depth. That is, lateral separation between various sensors will vary depending on the depths selected for the several probes introduced.

The invention is not to be deemed as limited to the herein described embodiments except as defined by the following claims.

The invention claimed is:

1. An assembly for providing access into the cranial cavity of a patient for a catheter borne sensor comprising:
   a single, solid, unitary body having a proximal end and a distal end;
   a threaded shank formed at the distal end of said unitary body for engaging the wall of a burr hole through the cranium of a patient;
   a plurality of lumens formed through the unitary body at skewed angles with respect to the axis of rotation of said shank and converging from locations radially outward from the axis of rotation and separated from each other in the proximal end of said unitary body toward the axis of rotation and each other to reach their closest proximity within said shank, wherein convergence of said lumens toward the axis and the angular skew of said lumens with respect to the axis are such that the distal ends of said lumens are nested to fit compactly together about the axis in said shank and are such that each lumen intersects the path that an adjacent lumen would take if such adjacent lumen were not skewed with respect to said axis of rotation, each lumen having a proximal end situated outside the cranial wall when the device is in use and a distal end accessing the interior of the cranial wall when the device is in use;
   one or more tubular guides attachable to said unitary body at the proximal end of one or more of said lumens for guiding a catheter borne sensor from the exterior of the cranial cavity to the proximal end of the one or more of said lumens;
   an introducer comprising a flexible hollow tube adapted to be inserted through at least one of the one or more tubular guides, through the lumen associated with said at least one of the one or more tubular guides and into brain tissue within the cranial cavity for facilitating the insertion of a delicate catheter borne sensor into the brain tissue within the cranial cavity: and
   a stylet adapted to extend through said flexible hollow tube for providing rigidity thereto during insertion of said flexible hollow tube through said one tubular guide and the associated lumen and further adapted to be withdrawn from said flexible hollow tube after insertion.

2. An assembly according to claim 1 further comprising a sharpened surface at the distal end of one of said stylet and said flexible hollow tube for opening the dura.

3. A system for providing access into the cranial cavity of a patient for a catheter borne sensor comprising:
   a single, solid, unitary body having a proximal end and a distal end;
   a threaded shank formed at the distal end of said unitary body for engaging the wall of a burr hole through the cranium of a patient;
   a plurality of lumens, wherein at least one of the lumens has a diameter unequal to the diameters of other lumens, said lumens being formed through the unitary body at angles skewed with respect to the axis of rotation of said shank and converging from locations radially outward from the axis of rotation and separated from each other in the proximal end of said unitary body toward the axis of rotation and each other to reach their closest proximity within said shank, wherein convergence of said lumens toward the axis and the angular skew of said lumens with respect to the axis are such that the distal ends of said lumens are nested to fit compactly together about the axis in said shank and are such that each lumen intersects the path that an adjacent lumen would take if such adjacent lumen were not skewed with respect to the axis of rotation, the angles of skew of at least one of lumens being unequal to the angles of skew of other lumens for optimizing the closeness of said lumens in the distal end of said shank and minimizing the diameter of said shank, each lumen having a proximal end situated outside the cranial wall when the device is in use and a distal end accessing the interior of the cranial wall when the device is in use; and one or more tubular guides attachable to said unitary body at the proximal end of one or more of said lumens for guiding a catheter borne sensor from the exterior of the cranial cavity to the proximal end of the one or more of said lumens..

4. A system according to claim 3 further comprising:

an introducer comprising a flexible hollow tube adapted to be inserted through at least one of the one or more tubular guides and the lumen associated with said at least one of the one or more tubular guides for facilitating the insertion into the cranial cavity of a delicate catheter borne sensor; and a stylet adapted to extend through said flexible hollow tube for providing rigidity thereto during insertion of said flexible hollow tube through said one tubular guide and the associated lumen and further adapted to be withdrawn from said flexible hollow tube after insertion .

5. A system according to claim 4 further comprising a sharpened surface at the distal end of one of said stylet and said flexible hollow tube for opening the dura.

* * * * *